United States Patent [19]

Christensen et al.

[11] 4,262,011
[45] Apr. 14, 1981

[54] 1-1-DISUBSTITUTED-PEN-2-em-3-CARBOXYLIC ACIDS

[75] Inventors: Burton G. Christensen, Scotch Plains; David H. Shih, Edison, both of N.J.

[73] Assignee: Merck & Co., Inc., Rahway, N.J.

[21] Appl. No.: 99,400

[22] Filed: Dec. 3, 1979

[51] Int. Cl.³ .................... C07D 487/04; A61K 31/40
[52] U.S. Cl. ................................ 424/274; 260/239 A; 260/245.2 T
[58] Field of Search .................. 260/245.2 T; 424/274

[56] References Cited

U.S. PATENT DOCUMENTS

| 4,181,733 | 1/1980 | Christensen et al. | 424/274 |
| 4,206,219 | 6/1980 | Christensen et al. | 424/274 |
| 4,208,422 | 6/1980 | Christensen et al. | 424/274 |

Primary Examiner—Mary C. Lee

Attorney, Agent, or Firm—James A. Arno; Julian S. Levitt

[57] ABSTRACT

Disclosed are 1-substituted-pen-2-em-3-carboxylic acids (I) and their pharmaceutically acceptable salts and esters which are useful as antibiotics; such compounds are prepared by total synthesis.

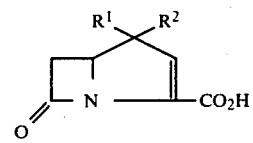

wherein $R^1$ and $R^2$ are, inter alia, substituted and unsubstituted alkyl, aryl, aralkyl, cycloalkyl, cycloalkylalkyl, and spirocycloalkyl.

6 Claims, No Drawings

1-1-DISUBSTITUTED-PEN-2-em-3-CARBOXYLIC ACIDS

BACKGROUND OF THE INVENTION

This invention relates to 1-substituted-pen-2-em-3-carboxylic acids(I) and their pharmaceutically acceptable salts and esters which are useful as antibiotics. This invention also relates to a process for preparing such compounds, (I):

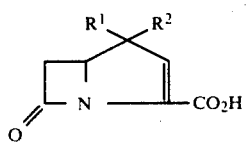

wherein $R^1$ and $R^2$ are selected from the group consisting of substituted and unsubstituted: loweralkyl having from 1-6 carbon atoms; aralkyl such as phenyloweralkyl; aryl such as phenyl; cycloalkyl having from 3-6 carbon atoms; and cycloalkylalkyl having 1-3 carbon atoms in the alkyl moiety and 3-6 carbon atoms in the ring; additionally, $R^1$ and $R^2$ may be joined together to form a spiro cyclic substituent at ring position number 1. Wherein said ring or chain substituents on $R^1$ and $R^2$ are selected from the group consisting of halo, such as chloro, bromo, fluoro and iodo, hydroxyl, amino, mono-, di-, and trialkylamino wherein the alkyl moiety has 1-6 carbon atoms; carboxyl, carbamoyl, amidino, guanidino, ureido, and the like.

There is a continuing need for new antibiotics. For unfortunately, there is no static effectiveness of any given antibiotic because continued wide scale usage selectively gives rise to resistant strains of pathogens. In addition, the new antibiotics suffer from the disadvantage of being effective only against certain types of microorganisms. Accordingly, the search for new antibiotics continues.

Thus, it is an objection of the present invention to provide a novel class of antibiotics (I) which are useful in animal and human therapy and in inanimate systems. These antibiotics are active against a broad range of pathogens which representatively include both gram positive bacteria such as *S. aureus, Strep. pyrogenes,* and *B. subtilis* and gram negative bacteria such as *E. coli, Proteus morganii,* Serratia, Pseudomonas and Klebsiella.

Further objects of this invention are to provide chemical processes for the preparation of such antibiotics and their non-toxic pharmaceutically acceptable salts and ester; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

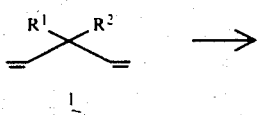

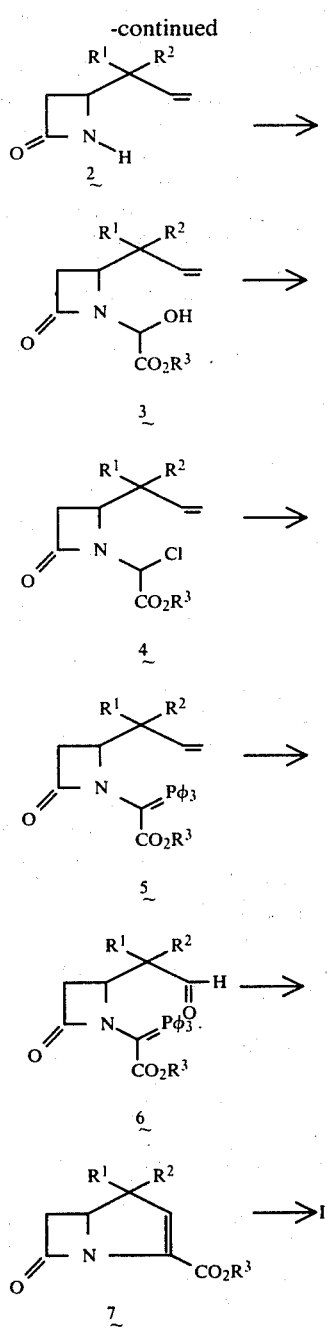

In words relative to the above diagram, the substituted azetidinone 2 is prepared by reacting a 3-substituted 1,4-pentadiene with chlorosulfonylisocyanate at 25° to 60° C. in a pressure bottle for 3-12 days, then the resulting mixture is hydrolyzed with aqueous sodium sulfite solution between pH 6.5-7.5 at 0° C. to 25° C. for from 5 min. to 60 min. The reaction 2→3 is accomplished by treating 2 in a solvent such as benzene, toluene, xylene, or the like at a temperature of from 80° to 130° C. for from 1 to 8 hours with a glyxoylate ester, $HCOCO_2R^3$, wherein $R^3$ is selected from the group consisting of readily removable carboxyl protecting groups, such as: o-nitrobenzyl, p-nitrobenzyl, o-dinitrobenzyl, benzyl or the like. In the alternative, $R^3$ may be a pharmaceutically acceptable ester moiety; in which case, the final deblocking (7→1) is not required. The halogenation reaction 3→4 may be conducted by any of a variety of well known halogenation means. Suitable reagents include SOCl₂, POCl₃, oxalyl chloride and the like. A preferred means of chlorination involves treating 3 in a solvent such as tetrahydrofuran (THF), ether, CH₂Cl₂, and the like with thionyl chloride in the presence of 1-2 equivalents (relative to the thionyl chloride) of base such as pyridine, triethylamine, quinoline and the like. Typically the reaction is conducted at a temperature of from −30° to 25° C. for from 0.5 to 1 hour. The resulting intermediate species 4 is isolated if desired by conventional procedure for later reaction, 4→5. Intermediate 5 is prepared from 4 by treating 4 in a solvent such as dimethylformamide (DMF), dimethylsulfoxide (DMSO), THF, dimethoxyethane (DME) or the like with 1 to 1.5 equivalents of a phosphine such as triphenylphosphine, tributylphosphine, triethylphosphine, tris-(2-cyanoethyl)phosphine or the like. Typically the reaction is conducted under a nitrogen atmosphere at a temperature of from 20° to 50° C., for from 0.5 to 2 hours. The reaction 5→6 may be achieved by any of a variety of well known oxidation reagents, such as RuO₄, OsO₄/NaIO₄, H₂O₂/Pb(OAc)₄, or O₃/Pφ₃. A particularly convenient means for the oxidating 5→6 is by treating 5 with ozone in a solvent such as methanol, trifluoroacetic acid or the like at a temperature of from −100° to 0° C., for from 0.1 to 4 hours, followed by treating the crude product with triphenyl phosphine at −18° C. to 0° C. for 0.1 to 2 hours. The closure step 6→7 is conducted at a temperature of from about 0° to 100° C. for from 0.25 to 24 hours in a solvent such as benzene, toluene, dioxane, xylene, or DMF. The carboxyl deblocking step 7→1 may be achieved by a number of well known procedures such as hydrolysis, hydrogenation, or photolysis of a suitable R³ group. Suitably hydrogenation catalysts for deblocking include the platinum metals and their oxides such as palladium on carbon and the like; suitable solvents for the hydrogenation include methanol, dioxane/H₂O, ethanol/H₂O, and the like in the presence of hydrogen at a pressure of from 1 to 50 atmospheres; the hydrogenation is typically conducted for from 5 min. to 4 hours at a temperature of about 25° C. in the optional presence of a mild base such as sodium bicarbonate or the like.

Typically, however, the carboxyl deblocking is achieved by photolysis of the o-nitrobenzyl ester of 7 (R³=o-nitrobenzyl) using 350 nm lamp in dioxane/H₂O in the presence of 1-2 equivalents of NaHCO₃ at 25° C. for 1-6 hours.

Preparation of Starting Material 1

With respect to starting reagent 1, its preparation is generally described in *J. Amer. Chem. Soc.*, 74, 661 (1952) by E. B. Reid and T. E. Gompf; *J. Org. Chem*, 23, 1063 (1958) by R. Ciola and K. L. Burwell, Jr.; and Belgium Patent 632,193 (1963) of R. Polster and E. Scharf. The following scheme summarizes the preparation of 1.

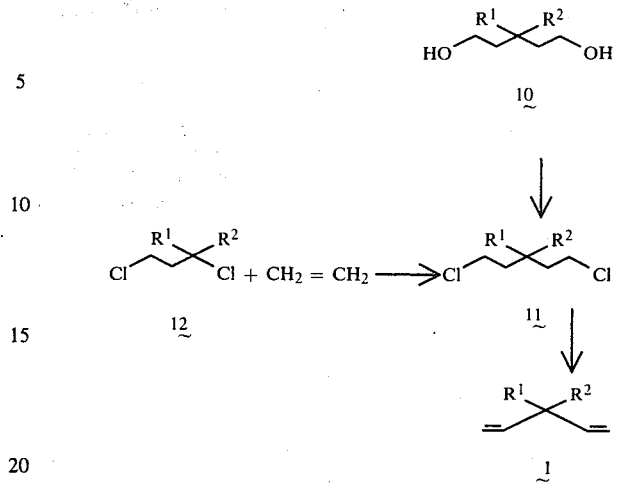

In words relative to the above scheme, the diester 9 is prepared by treating the diacid 8 with thionyl chloride at reflux for two hours followed by reacting with ethanol at 80° C. for 4 hours. Reduction of the diester 9 with lithium alumium hydride in ether at reflux for 4 hours followed by hydrolysis with 10% NaOH gives diol 10 which on further reaction with thionyl chloride, gives the dichloride 11. The dichloride 11 can be alternatively prepared by treating 12 with ethylene in the presence of alumium chloride. Treatment of the dichloride 11 with base such as 2-methylquinoline, DBU or sodium hydroxide in polyethylene glycol gives the expected 3-substituted 1,4-pentadiene 1.

Especially preferred embodiments of the present invention are those wherein R¹ and R² are selected from the group consisting of: methyl, ethyl, propyl, isopropyl, cyclopropyl, phenyl, benzyl, 2-bromoethyl, spirocyclopropyl. Also especially preferred from a process perspective are species (1) wherein either R¹ or R², but not both, are hydrogen.

The compounds made available by the present invention are valuable antibiotics active against various gram-positive and gram-negative bacteria and, accordingly, find utility in human and veterinary medicine. Such sensitive bacteria representatively include: *Staphylococcus aureus, Escherichia coli, Klebsiella pneumoniae*, Serratia, *Salmonella typhosa*, Pseudomonas and *Bacterium proteus*. The resulting compounds may further be utilized as additives to animal feed, for preserving foodstuffs, and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased paints and in the white water of paper mills to inhibit the growth of harmful bacteria.

These antibiotics may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, or syrups; or may be presented as a dry product, for reconstitution with water or other suitable vehicles before use. Such liquid preparations may contain conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid.

Compositions for injection may be presented in unit dose form in ampules, or in multidose container. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water before use.

The compositions may also be prepared in suitable forms for absorption through the mucous membranes of the nose and throat or bronchial tissues and may conveniently take the form of powder, liquid sprays, inhalants, lozenges, or throat paints. For medication of the eyes or ears, the preparations may be presented as individual capsules, in liquid or semi-solid form, or may be used as drops. Topical applications may be formulated in hydrophobic or hydrophilic bases as ointments, creams, or lotions.

Also, in addition to a carrier, the instant compositions may include other ingredients such as stabilizers, binders, antioxidants, preservatives, lubricators, suspending agents, viscosity agents or flavoring agents and the like. In addition, there may also be included in the compositions other active ingredients to provide a broader spectrum of antibiotic activity.

For veterinary medicine the composition may, for example, be formulated as an intramammary preparation in either long or quick-release bases.

The dosage to be administered depends to a large extent upon the general health and weight of the subject being treated, and the route and frequency of administration—the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lies in the range of from about 15 to 150 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferably to employ a dosage amount in the range of from about 100 mg to 1000 mg. In parenteral administration the unit dosage is usually the pure compound in a slightly acidified sterile water solution or in the form of a soluble powder intended for solution.

Especially preferred pharmaceutically acceptable salts and esters involving the carboxyl group of compounds of the present invention (I) are disclosed and claimed in co-pending U.S. Patent Application Ser. No. 861,314 (filed Dec. 16, 1977), now U.S. Pat. No. 4,181,733, which application is directed, inter alia, to pharmaceutically acceptable salts and esters of the carboxyl group of thienamycin. It is precisely these salts and esters which are preferred in the present invention and they are prepared in a manner analogous to that disclosed in U.S. Patent Application Ser. No. 861,341, which is incorporated herein by reference. Thus, especially preferred salts include sodium, potassium, ammonium, and the like; and especially preferred esters include pivaloxymethyl, p-t-butylbenzyl, 5-indanyl, 3-phthalidyl, 3-methyl-2-butenyl, and the like. One should note that when, in the total synthesis outlined above, $R^3$ is a pharmaceutically acceptable ester moiety, there is no need for the final deblocking step if it is desired to have the final product I in the form of a pharmaceutically acceptable ester.

The following Examples illustrate, but do not limit, the product, process or compositional aspects of the invention. All temperatures are in °C.

EXAMPLE 1

Preparation of 3,3-Dimethyl-1,4-pentadiene

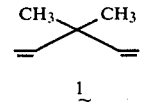

1

Procedure a $\beta,\beta$-Dimethylglutaric acid (obtained from Aldrich Chemical Company) (one mole), is refluxed for 2 hours with thionyl chloride (68% excess). After removal of excess thionyl chloride, absolute ethanol (109% excess) is added slowly. The mixture is refluxed for 3 hours then distilled to collect the product, diethyl $\beta,\beta$-dimethylglutarate (98% yield).

To a suspension of lithium aluminum hydride (24 g) in ether (860 ml) is added dropwise with rapid stirring a solution of diethyl $\beta,\beta$-dimethylglutarate (124 g in 250 ml ether). The mixture is refluxed for 6 hours, then cooled to room temperature. Water (25 ml) is added slowly. The mixture is then titrated with 10% NaOH until a clear organic layer is obtained. The organic layer is separated, dried over anhydrous sodium sulfate then evaporated in vacuo to give the resulting diol as an oil (90% yield), b.p. 95° at 1.0 mm. The 3,3-dimethyl-1,5-pentanediol (0.5 mole) is treated with thionyl chloride (1.05 mole) at reflux for 3 hours. After removal of excess thionyl chloride in vacuo, the 3,3-dimethyl-1,5-dichloropentane is obtained (90% yield).

3,3-Dimethyl-1.5-dichloropentane (41 g) is added dropwise at 170° C. to a mixture of 48 g of sodium hydroxide and 40 g of polyethylene glycol tetramer and the mixture is distilled to give 3,3-dimethyl-1,4-pentadiene (66%).

Procedure b

At −40° C., 1,3-dichloro-3-methylbutane (50 g) is mixed with aluminum chloride (5 g). The ethylene is bubbled through the mixture for 4 hours. The mixture is allowed to warm to room temperature and hydrolyzed with water. The mixture is extracted with ethyl acetate to give 3,3-dimethyl-1,5-dichloropentane.

A mixture of 0.5 mole of 3,3-dimethyl-1,5-dichloropentane, 2-methylquinoline (2 moles), and sodium iodide (0.1 mole) is refluxed in a flask equipped with a Vigreaux column at the top of which is a condenser and take-off. The diolefin 1 is collected during 8 hrs reaction. The product is dried over anhydrous sodium sulfate.

EXAMPLE 2

Preparation of 3-methyl-1,4-pentadiene

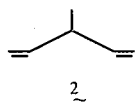

2

Following the procedure of Example 1(a), but replacing β,β-dimethylglutaric acid with an equivalent amount of β-methylglutaric acid, 3-methyl-1,4-pentadiene is obtained.

EXAMPLE 3

Preparation of 4-(1,1-dimethyl-pro-2-enyl)azetidin-2-one

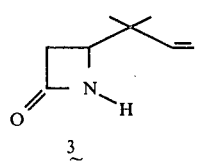

3

In a sealed tube, 3,3-dimethyl-1,4-pentadiene (9.6 g) and chlorosulfonyl isocyanate (14.2 g) are allowed to stand at room temperature for 6 days. The resulting mixture is diluted with methylene chloride and added slowly to a stirred aqueous solution which contains 20 g of Na$_2$SO$_3$ and 50 g of K$_2$HPO$_4$ at 0°–5° C. for 30 min. The organic layer is separated and dried over Mg$_2$SO$_4$. After evaporation, the crude product is chromatographed on silica gel GF eluting with EtOAc to give 3.

EXAMPLE 4

Preparation of 4-(1-methyl-pro-2-enyl)azetidin-2-one

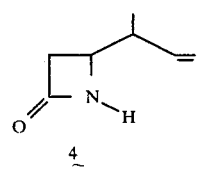

4

Following the procedure of Example 3, but replacing 3,3-dimethyl-1,4-pentadiene with 3-methyl-1,4-pentadiene, the title compound 4 is obtained.

EXAMPLE 5

Preparation of 4-(1,1-dimethyl-prop-2-enyl)-1-(1-hydroxy-1-o-nitrobenzoyloxycarbonylmethyl)-azetidin-2-one

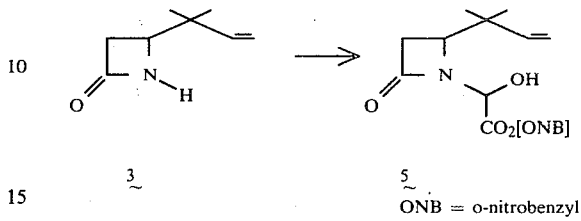

3         5

ONB = o-nitrobenzyl

The azetidinone 3 (0.5 g) and o-nitrobenzyl glyoxylate hydrate (1.5 g) are refluxed in benzene (100 ml) for 6 hrs. The reaction apparatus is equipped with a Dean-Stark trap for removal of water azeotropically. The solution is cooled, evaporated, and chromatographed on silica gel eluting with 50% EtOAc/cyclohexane to give product 5.

EXAMPLE 6

Preparation of 4-(1,1-Dimethyl-prop-2-enyl)-1-o-nitrobenzyloxycarbonyl-1-triphenylphosphoranylidenemethyl)-azetidin-2-one

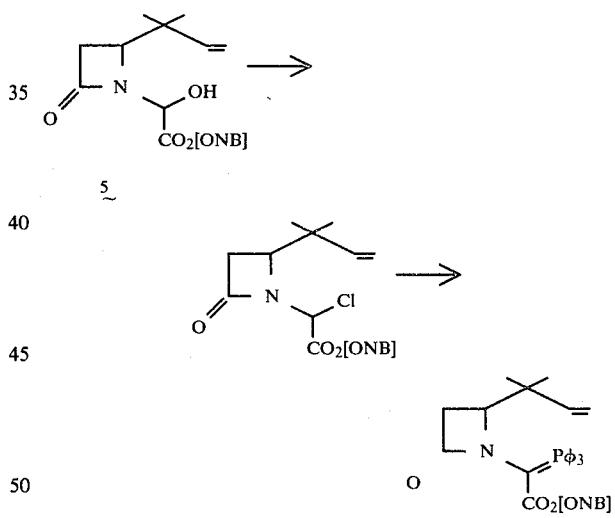

Under N$_2$, at −20° C., the carbinol 5 (0.5 g) in 5 ml THF is treated with thionyl chloride (204 mg) and pyridine (136 mg) for 10 min., then the mixture is allowed to warm to room temperature. The mixture is diluted with 10 ml benzene and filtered from solids. Evaporation of filtrate in vacuo gives the expected chloride which is then treated with triphenylphosphine (468 mg) in 5 ml DMF and stirred at room temperature for 4 hrs. After evaporation of solvent in vacuo, the residue is dissolved in 70 ml CH$_2$Cl$_2$ and washed with 0.5M sodium phosphate buffer (pH 6.9). The organic layer is separated, dried over MgSO$_4$ and chromatographed on silica gel eluting with 30% ethylacetate/CH$_2$Cl$_2$ to give 6.

EXAMPLE 7

Preparation of o-nitrobenzyl 1,1-dimethyl-1-carbapen-2-em-3-carboxylate

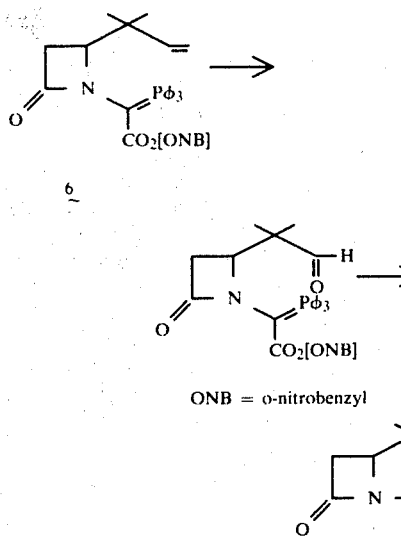

ONB = o-nitrobenzyl

The ylide 6 (7.0 mg in 0.7 ml ethyl acetate) is mixed with trifluoroacetic acid (16 mg) and cooled to $-78°$ C. Ozone is bubbled through the mixture until it is pale blue in color. Triphenylphosphine (3.7 mg) is added and nitrogen bubbled through the mixture for 10 min. The flask is transferred to an ice-bath and a saturated aqueous $NaHCO_3$ solution (1.0 ml) is added. After the mixture is stirred for 30 min under $N_2$, the organic layer is separated, dried over $MgSO_4$. The solution is left to stand at room temperature overnight, then evaporated and chromatographed on silica gel eluting with 50% EtOAc/cyclohexane to give 7.

EXAMPLE 7a

Preparation of 1,1-dimethyl-1-carbapen-2-em-3-carboxylic acid sodium salt

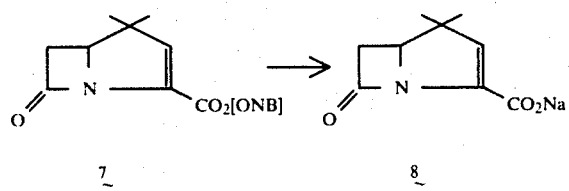

(a) A mixture of 7 (10 mg), 10% Pd/C (5 mg), and $NaHCO_3$ (5 mg) in dioxane/water/EtOH (1:1:0.1) (10 ml) is hydrogenated at 40 psi on the Parr shaker for 30 mins. The mixture is then filtered from catalyst. The filtrate is extracted with ether then the aqueous layer is separated, concentrated to 0.5 ml and lyophilized to give 8.

(b) A mixture of 7 (1 mg) in 1 ml 1:1 dioxane/water and 1 mg $NaHCO_3$ is photolyzed (350 nm) at room temperature for 1 hr. The mixture is extracted with ether. The aqueous layer is separated, concentrated to 0.2 ml and lyophilized to give 8.

EXAMPLE 8

Following the procedure of the foregoing Examples, the following azetidinones are obtained when the indicated change in reagents is made.

| | $R^1$ | $R^2$ |
|---|---|---|
| 1. | $CH_3$ | H |
| 2. | $CH_3$ | Et |
| 3. | Et | Et |
| 4. | $CH_3CH_2CH_2$ | $CH_3$ |
| 5. | $CH_3\!\!\diagdown\!\!CH\!\!\diagup\!\!CH_3$ | $CH_3$ |
| 6. | cyclopropyl | H |
| 7. | Ph—(ph = phenyl) | $CH_3$ |
| 8. | $PhCH_2$— | $CH_3$ |
| 9. | $R^1$ and $R^2$ are joined together to form a spiro-cyclopropyl | |
| 10. | $CH_2Br$ | $CH_3$ |

EXAMPLE 9

Following the procedure of Example 3 to 7a and utilizing the starting materials prepared in Example 8, the following representative species of present invention are obtained.

| | $R^1$ | $R^2$ | $R°$ |
|---|---|---|---|
| 1. | $CH_3$ | Et | Na |
| 2. | $CH_3CH_2$ | $CH_3$ | Na |
| 3. | $CH_3CH_2CH_2$ | $CH_3$ | Na |
| 4. | $CH_3$ | $CH_3$ | K |
| 5. | cyclopropyl | $CH_3$ | $-CH_2OCCMl_3$ (O) |
| 6. | phenyl | $CH_3$ | Na |
| 7. | $PhCH_2$ | $CH_3$ | $-CH_2-\!\!\bigcirc\!\!-$ |
| 8. | $BrCH_2CH_2CH_2$ | $CH_3$ | Na |
| 9. | $-CH_2-CH_2-$ | | Na |
| 10. | $CH_2NH_2$ | $CH_3$ | H |

EXAMPLE 11

Preparation of Pharmaceutical Compositions

One such unit dosage form is prepared by mixing 120 mg. of 1,1-dimethyl-pen-2-em-3-carboxylic acid with 20 mg of lactose and 5 mg of magnesium stearate. The 145 mg. mixture is placed into a No. 3 gelatin capsule. Similarly, by employing more of the active ingredient and less lactose, other dosage forms can be put up in No. 3 gelatin capsules and should it be necessary to mix more than 145 mg. of ingredients thereof, larger capsules such as compressed tablets and pills can also be prepared. The following examples are illustrative of the preparation of pharmaceutical formulations:

| TABLET | PER TABLET |
|---|---|
| 1,1-dimethyl-pen-2-em-3-carboxy acid | 125 mg. |
| Dicalcium Phosphate | 192 mg. |
| Cornstarch, U.S.P. | 6 mg. |
| Lactose, U.S.P. | 190 mg. |
| Magnesium Stearate | Balance |

The active ingredient is blended with the dicalcium phosphite, lactose and about half of the cornstarch. The mixture is then granulated with 15% cornstarch paste (6 mg) and rough-screened. It is dried at 45° C. and screened again through No. 16 screens. The balance of the cornstarch and the magnesium stearate is added and the mixture is compressed into tablets, approximately 0.5 inch in diameter each weighing 800 mg.

| PARENTERAL SOLUTION | |
|---|---|
| Ampoule: | |
| 1,1-dimethyl-pen-2-em-3-carboxylic acid | 500 mg. |
| Diluent: Sterile Water for Injection | 2 cc |
| OPTHALMIC SOLUTION | |
| 1,1-dimethyl-pen-2-em-3-carboxylic acid | 100 mg. |
| Hydroxypropylmethyl Cellulose | 5 mg. |
| Sterile Water | to 1 ml. |
| OTIC SOLUTION | |
| 1,1-dimethyl-pen-2-em-3-carboxylic acid | 100 mg. |
| Benzalkonium chloride | 0.1 mg. |
| Sterile Water | to 1 ml. |
| TOPICAL OINTMENT | |
| 1,1-dimethyl-pen-2-em-3-carboxylic acid | 100 mg. |
| Polyethylene Glycol 4000 U.S.P. | 400 mg. |
| Polyethylene Glycol 400 U.S.P. | 1.0 gram. |

What is claimed is

1. A compound having the formula:

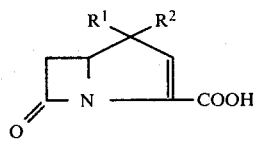

and its pharmaceutically acceptable salts and wherein $R^1$ and $R^2$ are selected from the group consisting of substituted and unsubstituted: loweralkyl having from 1-6 carbon atoms, phenyl, phenylloweralkyl, cycloalkyl having from 3 to 6 carbon atoms, cycloalkylalkyl having 1 to 7 carbon atoms in the chain and 3-6 carbon atoms in the ring and spirocycloalkyl having 3-6 carbon atoms; wherein said substituents on $R^1$ and $R^2$ are selected from the group consisting of halogen, hydroxyl, amino, and substituted amino, azido, cyano, carboxyl, alkoxyl, and mono-, di- and trialkylamino, each alkyl radical of the foregoing having 1-6 carbon atoms.

2. A compound according to claim 1 wherein $R^1$ and $R^2$ are selected from methyl, phenyl, ethyl, cyclopropyl, propyl, isopropyl, and spiro-cyclopropyl.

3. A compound according to claim 1 having the structure:

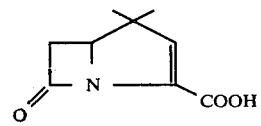

4. A compound according to claim 1 having the structure:

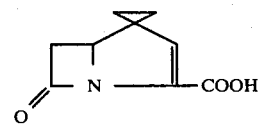

5. An antibiotic pharmaceutical composition comprising a therapeutically effective amount of a compound according to claims 1, 2, 3 or 4 and a pharmaceutical carrier therefor.

6. A method of treatment comprising administering an antibiotically effective amount of a compound according to claims 1, 2, 3, or 4.

* * * * *